(12) United States Patent
Sartor et al.

(10) Patent No.: US 10,869,716 B2
(45) Date of Patent: Dec. 22, 2020

(54) POWERED BIPOLAR RESECTOSCOPE

(71) Applicant: COVIDIEN LP, Mansfield, MA (US)

(72) Inventors: Joe D. Sartor, Longmont, CO (US); John A. Hammerland, III, Broomfield, CO (US); Jonathan P. Whittle, Cambridgeshire (GB)

(73) Assignee: Covidien LP, Mansfield, MA (US)

( * ) Notice: Subject to any disclaimer, the term of this patent is extended or adjusted under 35 U.S.C. 154(b) by 561 days.

(21) Appl. No.: 15/586,635

(22) Filed: May 4, 2017

(65) Prior Publication Data

US 2017/0231686 A1     Aug. 17, 2017

Related U.S. Application Data

(63) Continuation-in-part of application No. 15/163,766, filed on May 25, 2016, now Pat. No. 10,383,682.

(60) Provisional application No. 62/340,854, filed on May 24, 2016, provisional application No. 62/332,056, filed on May 5, 2016, provisional application No. 62/211,102, filed on Aug. 28, 2015.

(51) Int. Cl.
*A61B 18/14* (2006.01)
*A61B 18/00* (2006.01)
*A61B 18/12* (2006.01)
*A61B 34/30* (2016.01)

(52) U.S. Cl.
CPC ........ *A61B 18/149* (2013.01); *A61B 18/1485* (2013.01); *A61B 34/30* (2016.02); *A61B 2018/00184* (2013.01); *A61B 2018/00196* (2013.01); *A61B 2018/00208* (2013.01); *A61B 2018/00547* (2013.01); *A61B 2018/00559* (2013.01); *A61B 2018/00601* (2013.01); *A61B 2018/00922* (2013.01); *A61B 2018/00982* (2013.01); *A61B 2018/126* (2013.01)

(58) Field of Classification Search
CPC .............. A61B 18/149; A61B 18/1485; A61B 2018/00184; A61B 2018/00196; A61B 2018/00208; A61B 2018/00547
See application file for complete search history.

(56) References Cited

U.S. PATENT DOCUMENTS

| | | |
|---|---|---|
| 3,939,839 A | 2/1976 | Curtiss |
| 4,060,087 A | 11/1977 | Hiltebrandt et al. |
| 4,149,538 A | 4/1979 | Mrava et al. |
| 4,538,610 A | 9/1985 | Kubota |
| 4,726,370 A | 2/1988 | Karasawa et al. |

(Continued)

*Primary Examiner* — Michael F Peffley
*Assistant Examiner* — Bo Ouyang
(74) *Attorney, Agent, or Firm* — Carter, DeLuca & Farrell LLP

(57) ABSTRACT

An electrosurgical system includes a resectoscope and a generator. The resectoscope includes a fixed electrode, a movable electrode movable relative to the fixed electrode, and first and second switches actuated in first and second positions of the movable electrode, respectively. The generator is configured to supply energy to the fixed electrode and/or the movable electrode when the movable electrode is moving from the first position to the second position and to inhibit the supply of energy when the movable electrode is moving from the second position to the first position. The generator is configured to determine a direction of movement of the movable electrode based upon signals received from the first and second switches.

17 Claims, 10 Drawing Sheets

(56) References Cited

U.S. PATENT DOCUMENTS

| | | | |
|---|---|---|---|
| 4,744,361 | A | 5/1988 | Karasawa |
| 5,088,998 | A | 2/1992 | Sakashita et al. |
| 5,423,795 | A | 6/1995 | Eckert et al. |
| 5,423,813 | A | 6/1995 | Kaiser et al. |
| 5,634,924 | A | 6/1997 | Turkel et al. |
| 5,810,764 | A | 9/1998 | Eggers et al. |
| 5,857,962 | A | 1/1999 | Bracci et al. |
| 5,919,191 | A | 7/1999 | Lennox et al. |
| 5,993,445 | A | 11/1999 | Issa |
| 6,117,133 | A | 9/2000 | Zappala |
| 6,277,114 | B1 | 8/2001 | Bullivant et al. |
| 6,471,701 | B2 | 10/2002 | Brommersma et al. |
| 6,730,084 | B2 | 5/2004 | Held |
| 6,746,395 | B2 | 6/2004 | Brommersma et al. |
| 7,118,569 | B2 | 10/2006 | Snay et al. |
| 7,611,511 | B2 | 11/2009 | Blocher |
| 7,938,842 | B1 | 5/2011 | Chin |
| 2004/0242959 | A1 | 12/2004 | Nosel |
| 2006/0058580 | A1 | 3/2006 | Reichenbach et al. |
| 2011/0288573 | A1* | 11/2011 | Yates ............... A61B 17/07207 606/170 |
| 2011/0295066 | A1* | 12/2011 | Fan .................... A61B 1/00119 600/114 |
| 2012/0059219 | A1 | 3/2012 | St. George et al. |
| 2014/0236142 | A1 | 8/2014 | Ward et al. |
| 2014/0276795 | A1* | 9/2014 | Batchelor .......... A61B 18/1233 606/42 |
| 2015/0351826 | A1 | 12/2015 | Kroeber et al. |

\* cited by examiner

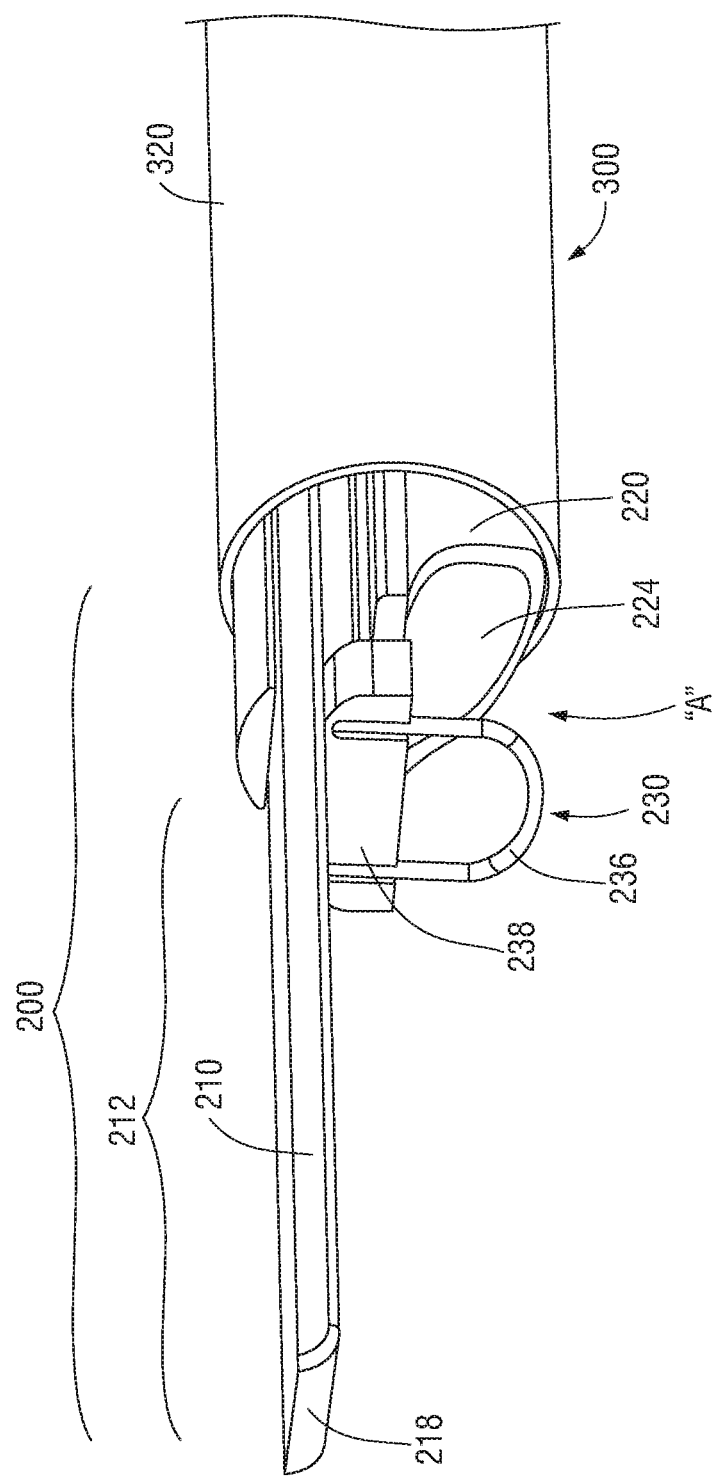

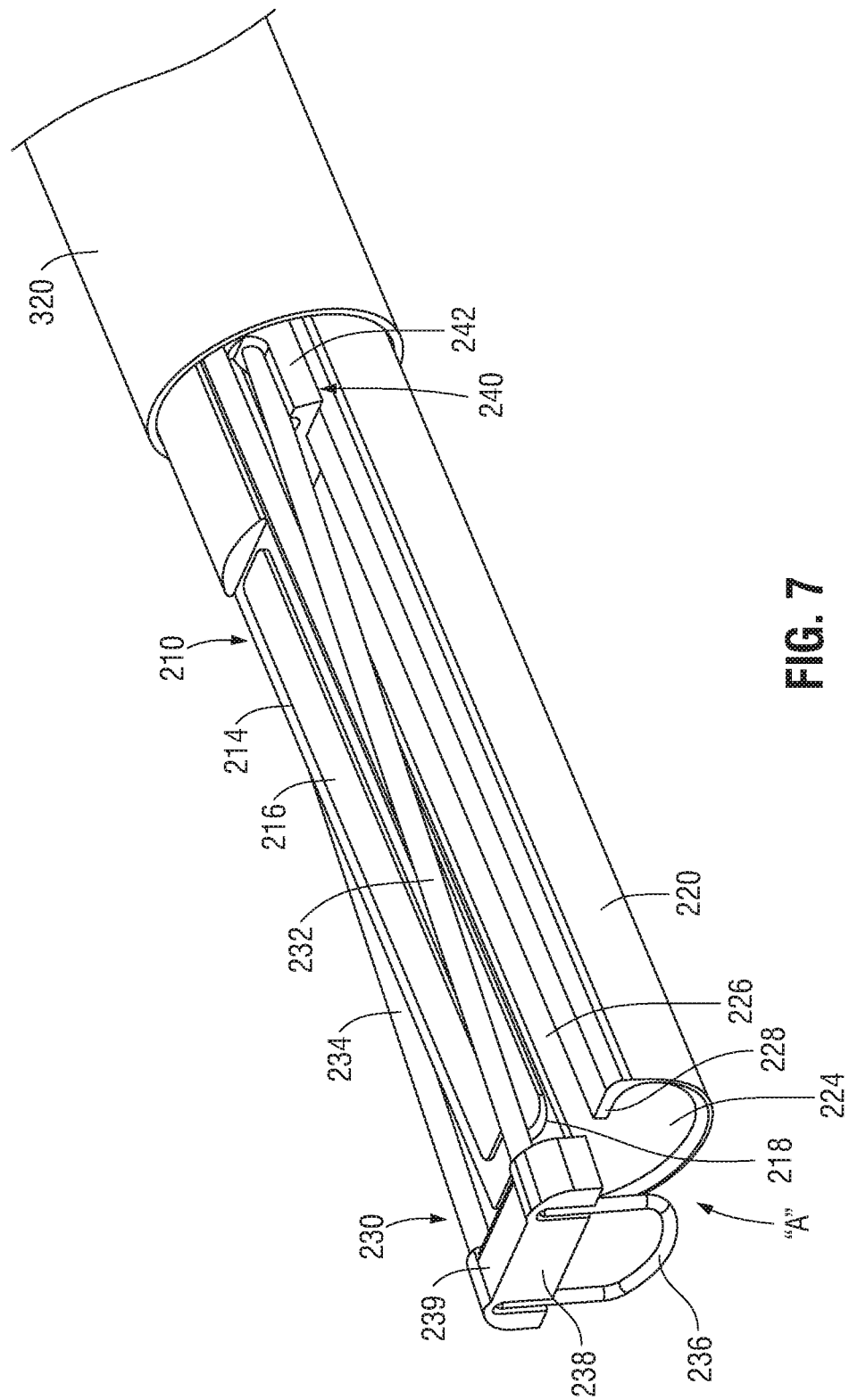

POWERED BIPOLAR RESECTOSCOPE

CROSS-REFERENCE TO RELATED APPLICATIONS

This application claims the benefit of U.S. Provisional Application No. 62/332,056, filed on May 5, 2016, and U.S. Provisional Application No. 62/340,854, filed on May 24, 2016, and is a continuation-in-part of U.S. application Ser. No. 15/163,766, filed on May 25, 2016, which claims the benefit of U.S. Provisional Application No. 62/211,102, filed on Aug. 28, 2015, the entire contents of each of which is hereby incorporated herein by reference.

BACKGROUND

Technical Field

The present disclosure relates to instruments for surgically resecting tissue and, more particularly, to a powered bipolar resectoscope for use in resecting tissue during prostate, intrauterine, and other surgical procedures.

Background of Related Art

A resectoscope is typically utilized during the course of a surgical procedure, e.g., a prostate or intrauterine surgical procedure, for removing tissue. Conventional resectoscopes include a handle, an endoscope extending from the handle, and one or more electrodes extending distally from the endoscope. The handle is provided for allowing the surgeon to manipulate e.g., extend and retract, the one or more electrodes relative to the endoscope. The endoscope enables the surgeon to view the surgical site. The one or more electrodes are configured to be energized and advanced through tissue to electrically resect tissue. The one or more electrodes may define a bipolar configuration or a monopolar configuration.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

In accordance with aspects of the present disclosure, a resectoscope is provided including an end effector assembly. The end effector assembly includes a fixed electrode, a movable electrode, and a spacer. The fixed electrode is adapted to connect to a first electrical potential and extends in a longitudinal direction. The movable electrode is adapted to connect to a second electrical potential and is biased transversely towards the fixed electrode. The spacer is coupled to the movable electrode. The movable electrode and the spacer are longitudinally movable relative to the fixed electrode between a first position, wherein the spacer is disposed between the fixed electrode and the movable electrode so as to maintain a spacing between the movable electrode and the fixed electrode against the bias of the movable electrode, and a second position, wherein the spacer is disposed distally of the fixed electrode, allowing the movable electrode to move transversely towards the fixed electrode under the bias of the movable electrode.

In an aspect of the present disclosure, the movable electrode includes a pair of longitudinal sections disposed within a plane and a U-shaped section. The U-shaped section interconnects the distal ends of the longitudinal sections and extends transversely relative to the plane of the longitudinal sections. The longitudinal sections are resiliently biased towards the fixed electrode, thereby biasing the movable electrode transversely towards the fixed electrode.

In another aspect of the present disclosure, the longitudinal sections are spaced-apart from one another and disposed on either side of the fixed electrode. In the second position of the movable electrode and the spacer, the longitudinal sections extend transversely beyond the fixed electrode on either side thereof.

In yet another aspect of the present disclosure, the end effector assembly further includes a longitudinally-extending shaft and a carrier engaging a proximal end of the movable electrode with the longitudinally-extending shaft such that movement of the longitudinally-extending shaft relative to the fixed electrode between a proximal position and a distal position moves the movable electrode and the spacer between the first and second positions.

In still another aspect of the present disclosure, an endoscope defining a field of view is disposed on the fixed electrode. In such aspects, the fixed electrode may further include an illumination assembly configured to illuminate the field of view of the endoscope.

In still yet another aspect of the present disclosure, the longitudinally-extending shaft defines a channel having an open distal end that is configured to receive resected tissue upon movement of the movable electrode and the spacer from the first position to the second position.

In another aspect of the present disclosure, the U-shaped section of the movable electrode is aligned with the longitudinally-extending shaft in the first position of the movable electrode, and is offset transversely relative to the longitudinally-extending shaft in the second position of the movable electrode.

In still another aspect of the present disclosure, the resectoscope further includes a drive assembly operably coupled to the longitudinally-extending shaft and a motor coupled to the drive assembly. The motor is configured to drive the drive assembly to move the longitudinally-extending shaft between a proximal position and a distal position.

In yet another aspect of the present disclosure, the drive assembly includes a lead screw defining a helical track and a collar disposed about the lead screw and operably coupled to the helical track such that rotation of the lead screw translates the collar about the lead screw. The motor is configured to rotate the lead screw to translate the collar about the lead screw, thereby moving the longitudinally-extending shaft between the proximal position and the distal position.

In still yet another aspect of the present disclosure, the helical track is continuous and wherein the motor is configured to drive rotation of the lead screw in a single direction to translate the collar about the lead screw from a proximal end of the lead screw to a distal end of the lead screw and back to the proximal end of the lead screw.

Another resectoscope provided in accordance with aspects of the present disclosure includes a housing, a drive assembly, a shaft, a movable electrode, and a fixed electrode. The drive assembly is disposed within the housing and includes a lead screw defining a helical track. A collar of the drive assembly is disposed about the lead screw and operably coupled to the helical track such that rotation of the lead screw translates the collar about the lead screw. The shaft is coupled to the collar and extends distally from the housing. Translation of the collar about the lead screw translates the shaft relative to the housing between a proximal position and a distal position. The fixed electrode is adapted to connect to a first electrical potential, is fixed relative to the housing, and extends distally from the housing alongside the shaft. The movable electrode is adapted to connect to a second electrical potential and is coupled to the shaft such that translation of the shaft relative to the housing between the proximal position and the distal position moves the movable electrode relative to the fixed electrode between a first position and a second position.

In an aspect of the present disclosure, a motor is disposed within the housing and configured to drive rotation of the lead screw.

In another aspect of the present disclosure, the helical track is continuous and the motor is configured to drive rotation of the lead screw in a single direction to translate the collar about the lead screw from a proximal end of the lead screw to a distal end of the lead screw and back to the proximal end of the lead screw.

In still another aspect of the present disclosure, the resectoscope further includes a sheath assembly. The sheath assembly includes a proximal base releasably engagable with the housing and an elongated sheath configured to at least partially surround the shaft, movable electrode, and fixed electrode.

In yet another aspect of the present disclosure, the proximal base of the sheath assembly includes a port adapted to connect to at least one of a source of suction or a source of irrigation for applying suction or irrigation, respectively, through the elongated sheath.

In still yet another aspect of the present disclosure, the movable electrode is movable longitudinally along the fixed electrode from the first position to an intermediate position and is movable both longitudinally and transversely relative to the fixed electrode from the intermediate position to the second position.

In another aspect of the present disclosure, the movable electrode is stationary relative to the shaft during movement of the movable electrode from the first position to the intermediate position and is movable transversely relative to the shaft during movement of the movable electrode from the intermediate position to the second position.

In yet another aspect of the present disclosure, the resectoscope further includes a carrier engaging the movable electrode with the shaft.

In another aspect of the present disclosure, an endoscope defining a field of view that extends at least partially between the fixed electrode and the shaft is provided.

In still another aspect of the present disclosure, the movable electrode includes a pair of longitudinal sections disposed within a plane and a U-shaped section. The U-shaped section interconnects distal ends of the longitudinal sections and extends transversely relative to the plane of the longitudinal sections.

In still yet another aspect of the present disclosure, in the first position of the movable electrode, the U-shaped section is aligned with the shaft. In the second position of the movable electrode, the U-shaped section is offset transversely relative to the shaft.

An electrosurgical system provided in accordance with aspects of the present disclosure includes a resectoscope and a generator. The resectoscope includes an end effector assembly including a fixed electrode and a movable electrode movable relative to the fixed electrode between a first position and a second position. The resectoscope further includes a switch assembly including a first switch and a second switch. The first switch is configured such that the first switch is actuated in the first position of the movable electrode, while the second switch configured such that the second switch is actuated in the second position of the movable electrode. The generator includes an energy source electrically coupled to the fixed electrode and the movable electrode, and a controller in communication with the switch assembly. The controller is configured to direct the energy source to supply energy to at least one of the fixed electrode or the movable electrode when the movable electrode is moving from the first position to the second position and to inhibit the supply of energy from the energy source to the at least one of the fixed electrode or the movable electrode when the movable electrode is moving from the second position to the first position. The controller is further configured to determine a direction of movement of the movable electrode based upon signals received from the first and second switches.

In an aspect of the present disclosure, the resectoscope further includes a motor configured to drive movement of the movable electrode between the first position and the second position. In such aspects, the generator may further include a power source electrically coupled to the motor and configured to power the motor.

In another aspect of the present disclosure, the resectoscope further includes a longitudinally-extending shaft operably coupled to the movable electrode such that movement of the longitudinally-extending shaft relative to the fixed electrode between a proximal position and a distal position moves the movable electrode between the first position and the second position.

In yet another aspect of the present disclosure, the resectoscope further includes a drive assembly having a lead screw defining a helical track and a collar disposed about the lead screw and operably coupled to the helical track such that rotation of the lead screw translates the collar about the lead screw. The collar is operably coupled to the longitudinally-extending shaft such that rotation of the lead screw moves the longitudinally-extending shaft between the proximal position and the distal position.

In still another aspect of the present disclosure, the helical track is continuous and the lead screw is configured to be rotated in a single direction to translate the collar about the lead screw from a proximal end portion of the lead screw to a distal end portion of the lead screw and back to the proximal end portion of the lead screw. The resectoscope may additionally or alternatively include a motor configured to drive rotation of the lead screw.

In still yet another aspect of the present disclosure, the resectoscope defines a longitudinal axis and the movable electrode is configured to move both longitudinally along and transversely relative to the longitudinal axis as the movable electrode is moved between the first position and the second position.

Another electrosurgical system provided in accordance with the present disclosure includes a resectoscope and a generator having a power source, an energy source, and a controller. The resectoscope includes a drive assembly operably coupled to the power source for enabling driving of the drive assembly. The resectoscope further includes a shaft coupled to the drive assembly, extending distally from the housing, and configured such that when the drive assembly is driven, the shaft translates relative to the housing between a proximal position and a distal position. The resectoscope additionally includes a fixed electrode operably coupled to a first electrical potential of the energy source and fixed relative to the housing, and a movable electrode operably coupled to a second electrical potential of the energy source.

The movable electrode is coupled to the shaft such that translation of the shaft relative to the housing between the proximal position and the distal position moves the movable electrode relative to the fixed electrode between a first position and a second position. The controller is configured to permit the energy source to supply energy to the fixed and movable electrodes upon translation of the shaft from the proximal position to the distal position and to inhibit the supply energy to the fixed and movable electrodes upon translation of the shaft from the distal position to the proximal position.

In an aspect of the present disclosure, the resectoscope further includes a switch assembly. In such aspects, the controller is configured to determine a direction of movement of the shaft based upon signals received from the switch assembly.

In another aspect of the present disclosure, the switch assembly includes a proximal switch and a distal switch. The proximal switch is configured such that the proximal switch is actuated in the proximal position of the shaft, while the distal switch configured such that the distal switch is actuated in the distal position of the shaft.

In still another aspect of the present disclosure, the drive assembly includes a motor that is powered by the power source.

In yet another aspect of the present disclosure, the resectoscope defines a longitudinal axis and the movable electrode is configured to move both longitudinally along the longitudinal axis and transversely relative to the longitudinal axis as the movable electrode is moved between the first position and the second position.

Another resectoscope provided in accordance with aspects of the present disclosure includes a housing, a drive assembly disposed within the housing and including a collar, a motor disposed within the housing and configured to move the collar between a proximal position and a distal position, a switch assembly disposed within the housing and including a proximal switch and a distal switch, a fixed electrode, and a movable electrode. The proximal switch is configured such that the collar actuates the proximal switch in the proximal position of the collar, while the distal switch is configured such that the collar actuates the distal switch in the distal position of the collar. The fixed electrode is adapted to connect to a first electrical potential and is fixed relative to the housing. The movable electrode is adapted to connect to a second electrical potential and is coupled to the collar such that translation of the collar relative to the housing between the proximal position and the distal position moves the movable electrode relative to the fixed electrode between a first position and a second position. The proximal and distal switches control supply of energy to the fixed and movable electrodes such that energy is permitted to be supplied to the fixed and movable electrodes when the movable electrode is moving from the first position to the second position and energy is inhibited from being supplied to the fixed and movable electrodes when the movable electrode is moving from the second position to the first position.

In an aspect of the present disclosure, a longitudinally-extending shaft is operably coupled between the collar and the movable electrode and configured to move the movable electrode upon movement of the collar.

In another aspect of the present disclosure, the drive assembly further includes a lead screw defining a helical track. The collar is disposed about the lead screw and operably coupled to the helical track such that rotation of the lead screw translates the collar about the lead screw. In aspects, the helical track is continuous and the lead screw is configured to be rotated in a single direction to translate the collar about the lead screw from a proximal end portion of the lead screw to a distal end portion of the lead screw and back to the proximal end portion of the lead screw.

In another aspect of the present disclosure, the resectoscope defines a longitudinal axis and the movable electrode is configured to move both longitudinally along the longitudinal axis and transversely relative to the longitudinal axis as the movable electrode is moved between the first position and the second position.

BRIEF DESCRIPTION OF THE DRAWINGS

Various aspects and features of the present disclosure are described herein with reference to the drawings wherein:

FIG. 5A is a perspective view of the distal end of the resectoscope of FIG. 1, disposed in a first position;

FIG. 7 is a top, perspective view of the distal end of the resectoscope of FIG. 1, disposed in the second position;

DETAILED DESCRIPTION

Figure 1:
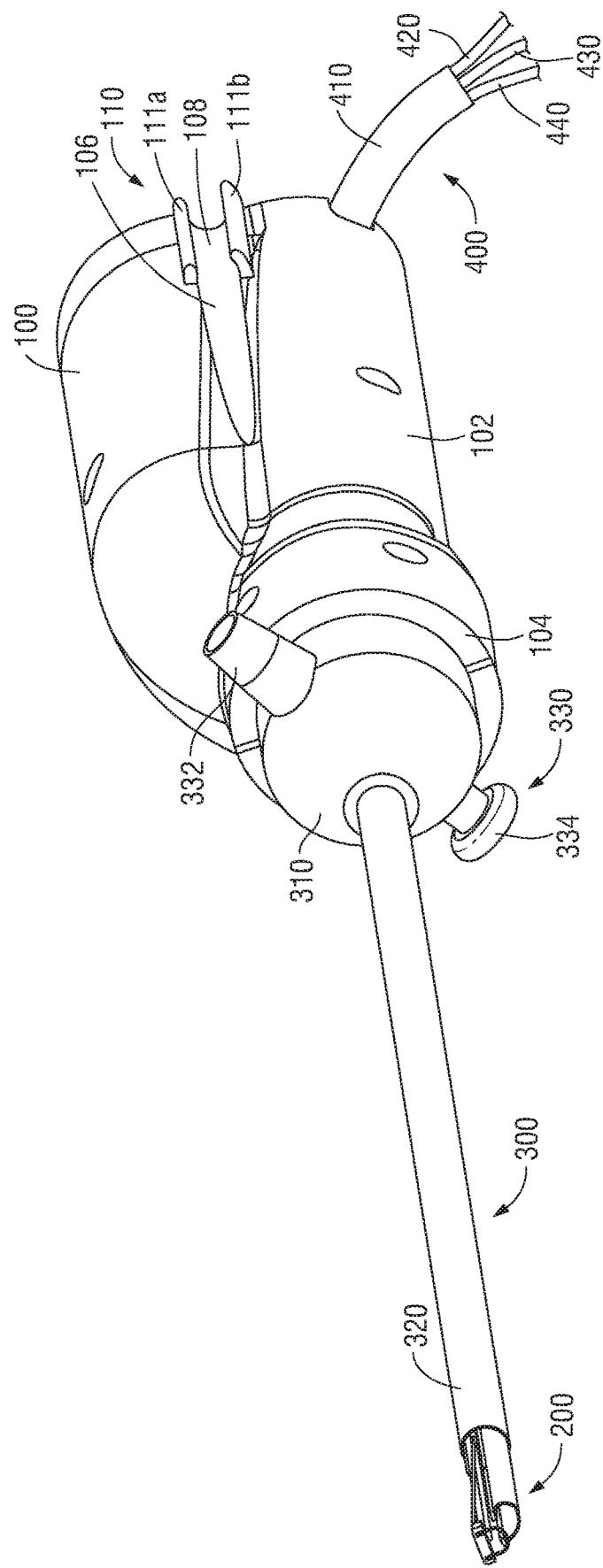
FIG. 1 is a perspective view of a resectoscope provided in accordance with the present disclosure.

Referring to FIGS. 1-4, provided in accordance with the present disclosure is a resectoscope identified by reference numeral 10. Resectoscope 10 generally includes a housing 100, an end effector assembly 200 extending distally from housing 100, a sheath assembly 300 releasably engageable with housing 100 and configured for positioning about at least a portion of end effector assembly 200, and a cable assembly 400. As detailed below, resectoscope 10 is configured as a bipolar electrosurgical resection and removal apparatus for use in prostate, intrauterine, and/or other surgical procedures, although resectoscope 10 may alternatively be configured for use with monopolar energy or other forms of energy, e.g., light energy, thermal energy, ultrasonic energy, etc.

Housing 100 includes a body portion 102 and a distal nose 104 disposed at the distal end of body portion 102. Body portion 102 of housing 100 encloses the internal operable components of resectoscope 10, as detailed below, and includes a guide 106 defined on the exterior surface thereof. Guide 106 includes a channel 108 defined within the exterior surface of body portion 102 and a clip 110 having first and second arms 111a, 111b disposed on either side of channel 108 and extending outwardly from the exterior surface of body portion 102. Guide 106 is configured to releasably secure a fluid line (not shown) therein to maintain the fluid line (not shown) in position extending along housing 100. Such a configuration inhibits the fluid line (not shown) from becoming tangled and/or interfering with the manipulation and operation of resectoscope 10.

Distal nose 104 of housing 100 includes a distal ring 112 having a pair of opposed posts 114 extending inwardly therefrom. Distal ring 112 and posts 114 are configured to facilitate releasable engagement of sheath assembly 300 with housing 100. More specifically, proximal base 310 of sheath assembly 300 defines a cylindrical portion 312 having a diameter slightly less than that of distal ring 112 of distal nose 104 of housing 100 to enable insertion of cylindrical portion 312 of proximal base 310 of sheath assembly 300 at least partially into distal ring 112 of distal nose 104 of housing 100. Cylindrical portion 312 further defines a pair of opposed L-shaped slots 314 configured to receive posts 114 of distal ring 112 upon insertion of cylindrical portion 312 of proximal base 310 into distal ring 112. Once inserted in this manner, proximal base 310 of sheath assembly 300 may be rotated relative to distal ring 112 of distal nose 104 of housing 100 to couple sheath assembly 300 with housing 100 via a bayonet-style engagement. Alternatively, other suitable releasable engagements may be provided, e.g., snap-fit, friction-fit, threaded coupling, etc.

Figure 2:
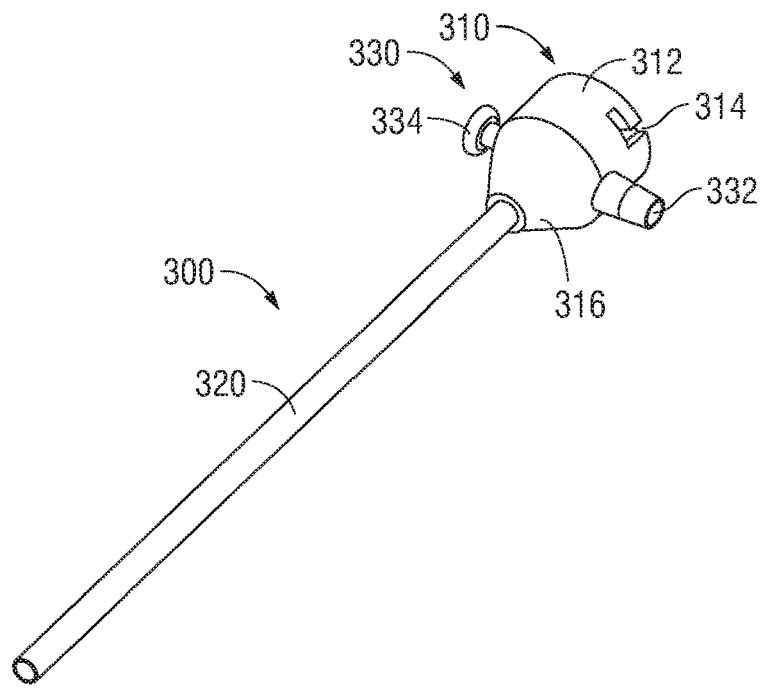
FIG. 2 is a perspective view of a sheath assembly of the resectoscope of FIG. 1.
Figure 3:
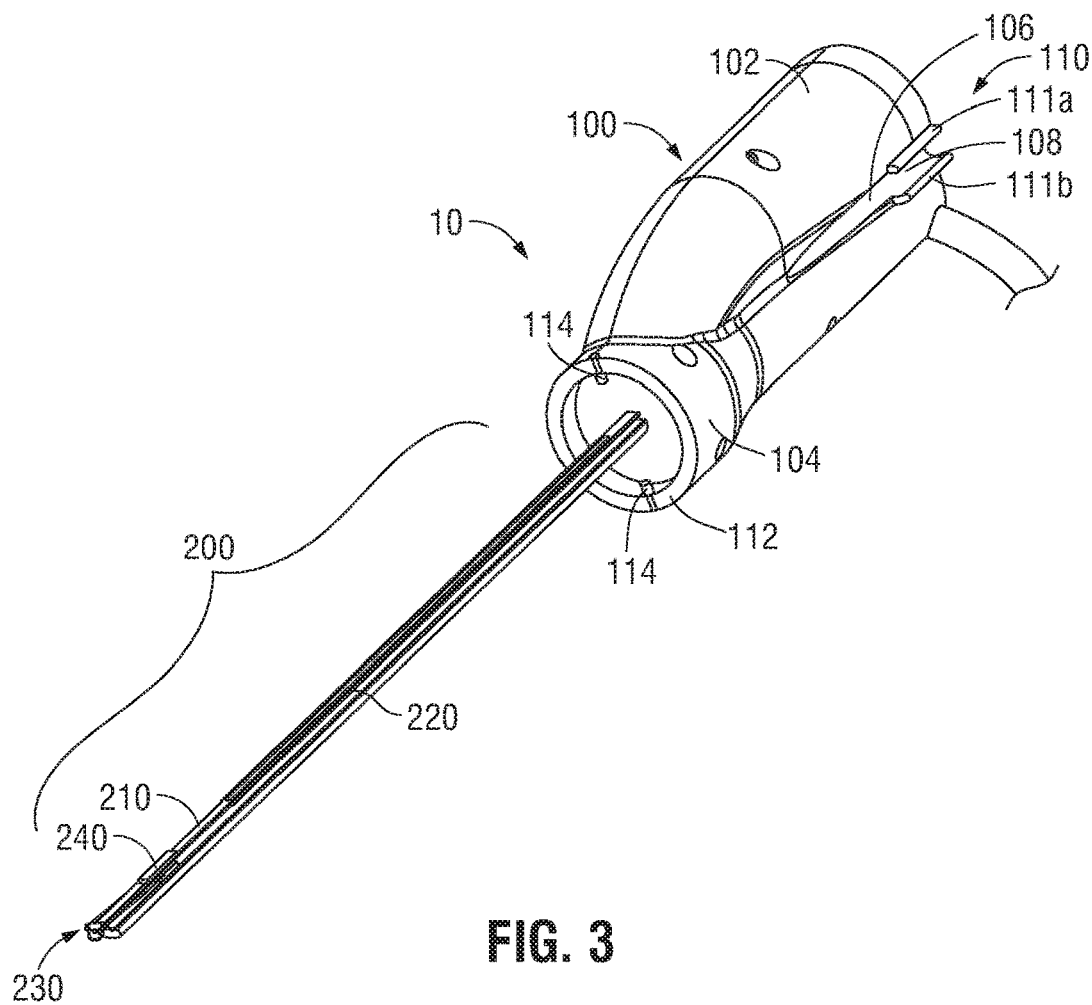
FIG. 3 is a perspective view of the resectoscope of FIG. 1 with the sheath assembly removed therefrom.

Referring to FIG. 2, sheath assembly 300, as mentioned above, includes proximal base 310 including a cylindrical portion 312 configured to releasably engage distal nose 104 of housing 100. Proximal base 310 further includes a conical portion 316 extending distally from cylindrical portion 312. An elongated tubular sheath 320 extends distally from conical portion 316 of proximal base 310. As detailed below, elongated tubular sheath 320 is configured to slidably receive shaft 220 and movable electrode 230 of end effector assembly 200 (FIG. 3). Sheath assembly 300 further includes a valve assembly 330 including a port 332 that selectively communicates with the interior of proximal base 310 and elongated tubular sheath 320, and a knob 334 associated with an internal valve (not shown) to enable a user to manually transition valve assembly 330 between an open condition, wherein port 332 communicates with the interior of proximal base 310 and elongated tubular sheath 320 to permit fluid flow therebetween, and a closed condition, wherein fluid flow through port 332 is inhibited. Port 332 may be configured to receive a fluid line (not shown), e.g., via friction-fit engagement about port 332, for applying irrigation and/or aspiration through elongated tubular sheath 320. As noted above, the fluid line (not shown) may be releasably secured within guide 106 of housing (FIG. 1) to inhibit tangling or interference.

Figure 4:
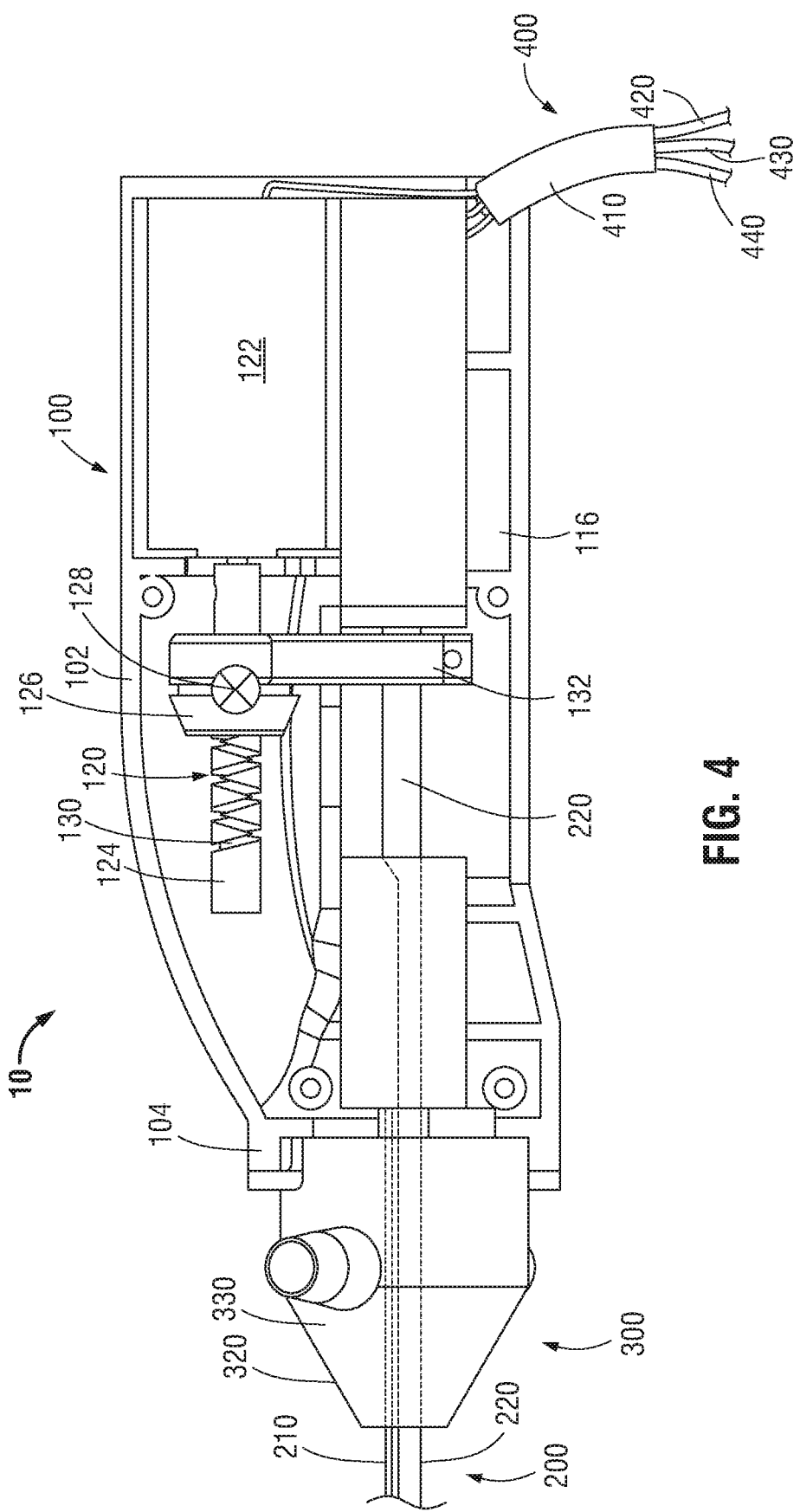
FIG. 4 is a side view of the proximal end of the resectoscope of FIG. 1 with a portion of the housing removed to illustrate the internal components thereof.
Figure 5B:
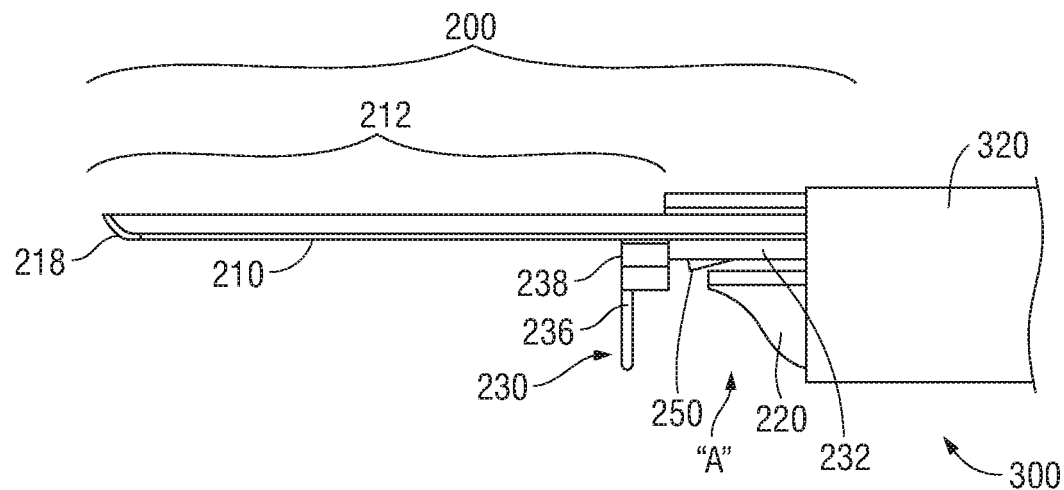
FIG. 5B is a side view of the distal end of the resectoscope of FIG. 1, disposed in the first position.
Figure 5C:
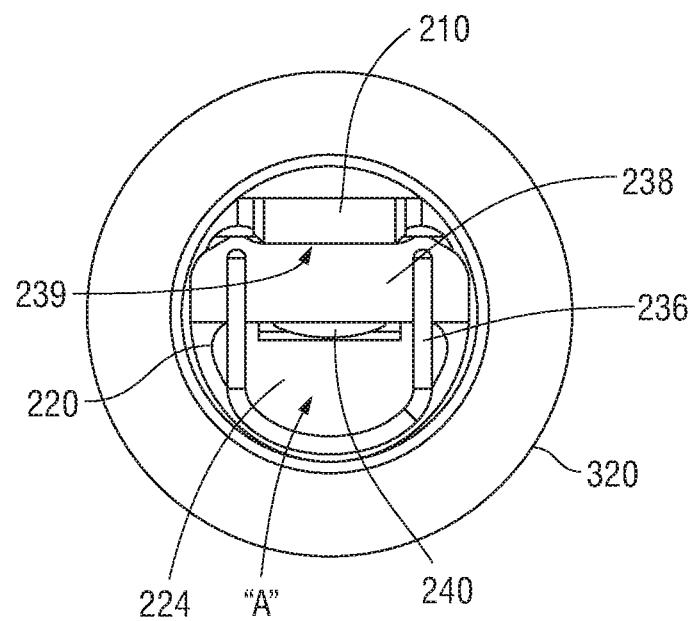
FIG. 5C is a distal end view of the distal end of the resectoscope of FIG. 1, disposed in the first position.

With reference to FIG. 4, housing 100 encloses an interior cavity 116 configured to house a drive assembly 120 and operably support the proximal end of end effector assembly 200. Drive assembly 120 includes a motor 122, a lead screw 124, a collar 126, and a pin 128. Motor 122 is operably coupled to lead screw 124 and configured to drive rotation of lead screw 124. Lead screw 124 defines a helical track 130 extending along at least a portion of the length thereof. Collar 126 is slidably disposed about lead screw 124. Pin 128 includes a first end that is coupled to collar 126 and a second end that is operably disposed within helical track 130 defined within lead screw 124 such that, upon rotational driving of lead screw 124 via motor 122, pin 128 is moved through helical track 130 to thereby translate collar 126 about lead screw 124 and relative to housing 100. Collar 126 of drive assembly 120 further includes a foot 132 that extends therefrom, as detailed below.

Lead screw 124 may be configured as a continuous lead screw 124 such that motor 122 need only drive lead screw 124 in a single direction. In such a configuration, once collar 126 has been translated to the distal end of helical track 130, further driving of motor 122 in the same direction returns collar 126 proximally back towards the proximal end of helical track 130. Likewise, once collar 126 has been translated to the proximal end of helical track 130, further driving of motor 122 in the same direction returns collar 126 distally back towards the distal end of helical track 130. Alternatively, where lead screw 124 is not a continuous lead screw 124, motor 122 may be configured to operate in a forward mode, wherein lead screw 124 is driven to rotate in a first direction to urge collar 126 to translate distally about lead screw 124 and relative to housing 100, and a reverse mode, wherein lead screw 124 is driven to rotate in a second, opposite direction to urge collar 126 to translate proximally about lead screw 124 and relative to housing 100.

An actuator (not shown) may be mounted on the exterior of housing 100 and coupled to motor 122 to enable selective activation of motor 122. With regard to configurations including a forward and reverse-drive motor 122, the actuator may be configured as a rocker switch, for example, to enable selective activation of motor 122 in each of the forward and reverse modes. With regard to configurations including a single-direction drive motor 122, the actuator may be a push-button switch. Other suitable actuators, either on housing 100 or remote therefrom, e.g., on generator 500 (FIGS. 8A and 8B), provided on a footswitch (not shown), etc. may alternatively be provided.

Referring to FIGS. 1, 3, and 4-7, end effector assembly 200 includes a plank 210, a shaft 220, a movable electrode 230, and a carrier assembly 240. Plank 210 is formed from, coated with, or otherwise includes an electrically-conductive material disposed thereon and/or therein to allow plank 210 to serve as the fixed electrode of end effector assembly 200. Plank 210 defines a proximal end that is fixedly engaged within housing 100 and extends distally from housing 100 through elongated tubular sheath 320 of sheath assembly 300 (when sheath assembly 300 is engaged with housing 100). An exposed distal portion 212 of plank 210 extends distally from sheath assembly 300. An elongated cut-out 214 defined transversely through distal portion 212 of plank 210 is configured to receive an LED assembly 216 (FIG. 7), e.g., a longitudinal array of LED's mounted within a casing, to illuminate the area between distal portion 212 of plank 210 and shaft 220, as detailed below. Alternatively, the LED assembly 216 (FIG. 7) may be mounted underneath plank 210 or in any other suitable position with or without a cut-out 214 defined within plank 210. In some embodiments, plank 210 may define a generally rectangular cross-sectional configuration, with the distal end thereof inducing a rounded lip 218. As detailed below, rounded lip 218 defines a guide surface configured to guide movement of movable electrode 230 relative to plank 210.

Plank 210 further includes endoscope 250 engaged therewith and depending therefrom. Endoscope 250 is oriented in a distal-facing direction and may be angled relative to shaft 220 so as to define a field of view encompassing the area surrounding U-shaped loop section 236 of movable electrode 230, the area disposed between the distal ends of plank 210 and shaft 220, and/or the area distally adjacent shaft 220. Endoscope 250 is configured to obtain video and/or still images of its field of view for output to an external display monitor, thus enabling a surgeon to visualize the tissue resection process, as detailed below. LED assembly 216 (FIG. 7) is operably positioned relative to endoscope 250 to illuminate the field of view of endoscope 250 to facilitate visualization thereof.

Shaft 220 of end effector assembly 200 defines a proximal end disposed within housing 100. Shaft 220 extends distally from housing 100 through elongated tubular sheath 320 of sheath assembly 300 (when sheath assembly 300 is engaged with housing 100). The proximal end of shaft 220 is engaged with foot 132 of collar 126 of drive assembly 120. As a result of this configuration, translation of collar 126 about lead screw 124 and relative to housing 100, e.g., via the rotational driving of lead screw 124 imparted thereto via motor 122, likewise translates foot 132 and, thus, shaft 220 relative to housing 100 and sheath assembly 300. More specifically, shaft 220 is translatable relative to housing 100 and sheath assembly 300 between a proximal position, wherein the distal end of shaft 220 is disposed within or protrudes a first distance from the distal end of elongated tubular sheath 320, and a distal position, wherein the distal end of shaft 220 extends distally from the distal end of elongated tubular sheath 320 a second, larger distance. As detailed below, movable electrode 230 and carrier assembly 240 are movable in conjunction with shaft 220 and relative to plank 210 and elongated tubular sheath 320 between a retracted position of end effector assembly 200 (FIGS. 5A-5C), corresponding to the proximal position of shaft 220, and an extended position of end effector assembly 200 (FIGS. 6A-7), corresponding to the distal position of shaft 220.

Shaft 220 defines an open distal end, a U-shaped cross-sectional configuration, and a channel 224 extending longitudinally therethrough. Channel 224 communicates with an elongated mouth 226 that extends longitudinally along at least a portion of shaft 220. Shaft 220 is oriented to extend along plank 210 such that elongated mouth 226 of channel 224 opposes the bottom surface of plank 210. Elongated mouth 226 is defined between a pair of longitudinal shelves 228 of shaft 220 that extend along at least a portion of the length of shaft 220. Shelves 228 narrow elongated mouth 226 such that elongated mouth 226 defines a width that is less than a width of channel 224. Via channel 224, suction may be applied through shaft 220 from the proximal end thereof to enable the withdrawal of fluids and/or resected tissue.

With reference to FIGS. 5A-7, movable electrode 230 is formed from one or more electrically-conductive wire segments and includes a pair of spaced-apart longitudinal sections 232, 234 interconnected at their distal ends by a U-shaped loop section 236. U-shaped loop section 236 extends transversely relative to longitudinal sections 232, 234 and, in some embodiments, may extend orthogonally relative to longitudinal sections 232, 234. Longitudinal sections 232, 234 are spaced-apart a distance greater than the width of plank 210, thus enabling plank 210 to pass therebetween, as detailed below. Longitudinal sections 232, 234 are formed from a resilient material and are biased towards an at-rest position, wherein longitudinal sections 232, 234 are angled upwardly such that the distal portions thereof extend above plank 210 and at least portion of U-shaped loop section 236 extends above plank 210, as detailed below.

A spacer 238 is disposed about the distal ends of longitudinal sections 232, 234 of movable electrode 230 adjacent U-shaped loop section 236. In the retracted position of end effector assembly 200 and during movement of end effector assembly 200 from the retracted position towards the extended position, spacer 238 is configured to maintain the distal end of movable electrode 230 in spaced-apart relation relative to plank 210, against the bias of resilient longitudinal sections 232, 234. More specifically, spacer 238 defines a cut-out 239 that, as a result of the resilient configuration of longitudinal sections 232, 234 of movable electrode 230, is biased to slidably receive a portion of plank 210 so as to guide translation of movable electrode 230 relative to plank 210 as end effector assembly 200 is moved from the retracted position to the extended position. In the extended position of end effector assembly 200, spacer 238 is positioned distally of plank 210, allowing movable electrode 230 to resiliently return, under bias, towards its at-rest position, wherein the distal portions of longitudinal sections 232, 234 extend above plank 210 and at least portion of U-shaped loop section 236 extends above plank 210. Spacer 238 is further configured to electrically-isolate movable electrode 230 from plank 210 and may be formed at least partially from an insulative material to achieve this purpose.

In addition or as an alternative to having resilient longitudinal sections 232, 234 that enable transverse movement of movable electrode 230 as end effector assembly 200 is moved from the retracted position to the extended position, movable electrode 230 may be associated with a lever or ramp to enable or facilitate transverse movement thereof upon movement of end effector assembly 200 from the retracted position to the extended position.

Continuing with reference to FIGS. 5A-7, carrier assembly 240 is disposed between shaft 220 and plank 210 and is engaged with shaft 220 at a position proximally-spaced from the distal end of shaft 220. Carrier assembly 240 includes a base 242 that receives the proximal ends of longitudinal sections 232, 234 of movable electrode 230 in fixed engagement therewith. More specifically, the proximal ends of longitudinal sections 232, 234 of movable electrode 230 are engaged with base 242 of carrier assembly 240 such that, in their at-rest position, longitudinal sections 232, 234 are angled upwardly towards plank 210. Base 242 is positioned relative to shaft 220 such that spacer 238 and U-shaped loop section 236 of movable electrode 230 are distally-spaced from the distal end of shaft 220.

As detailed above, carrier assembly 240 is engaged with shaft 220, the proximal ends of longitudinal sections 232, 234 of movable electrode 230 are engaged with carrier assembly 240, and plank 210 is fixed relative to housing 100. As such, translation of shaft 220 relative to housing 100 effects translation of shaft 220, carrier assembly 240, and movable electrode 230 relative to sheath assembly 300 and plank 210. In particular, with reference to FIGS. 5A-5C, in the retracted position of end effector assembly 200, shaft 220 is disposed in its proximal position within or protruding a small distance from sheath assembly 300, movable electrode 230 and carrier assembly 240 are disposed within sheath assembly 300, and the fixed plank 210 extends distally from sheath assembly 300. As a result of this configuration, in the retracted position of end effector assembly 200, spacer 238 is disposed between plank 210 and movable electrode 230 to urge movable electrode 230 away from plank 210 and towards shaft 220, against the resilient bias of movable electrode 230. In this position, movable electrode 230 is positioned such that U-shaped loop section 236 of movable electrode 230 is aligned with U-shaped shaft 220. As mentioned above, U-shaped loop section 236 of movable electrode 230 is distally-spaced from the distal end of shaft 220. Thus, in the retracted position of end effector assembly 200, an area "A" having a U-shaped cross-sectional configuration extending distally from shaft 220 through U-shaped loop section 236 and within the peripheral boundaries defined by U-shaped loop section 236 and shaft 220 is defined. Area "A" is at least partially contiguous with channel 224 of shaft 220.

Figure 6A:
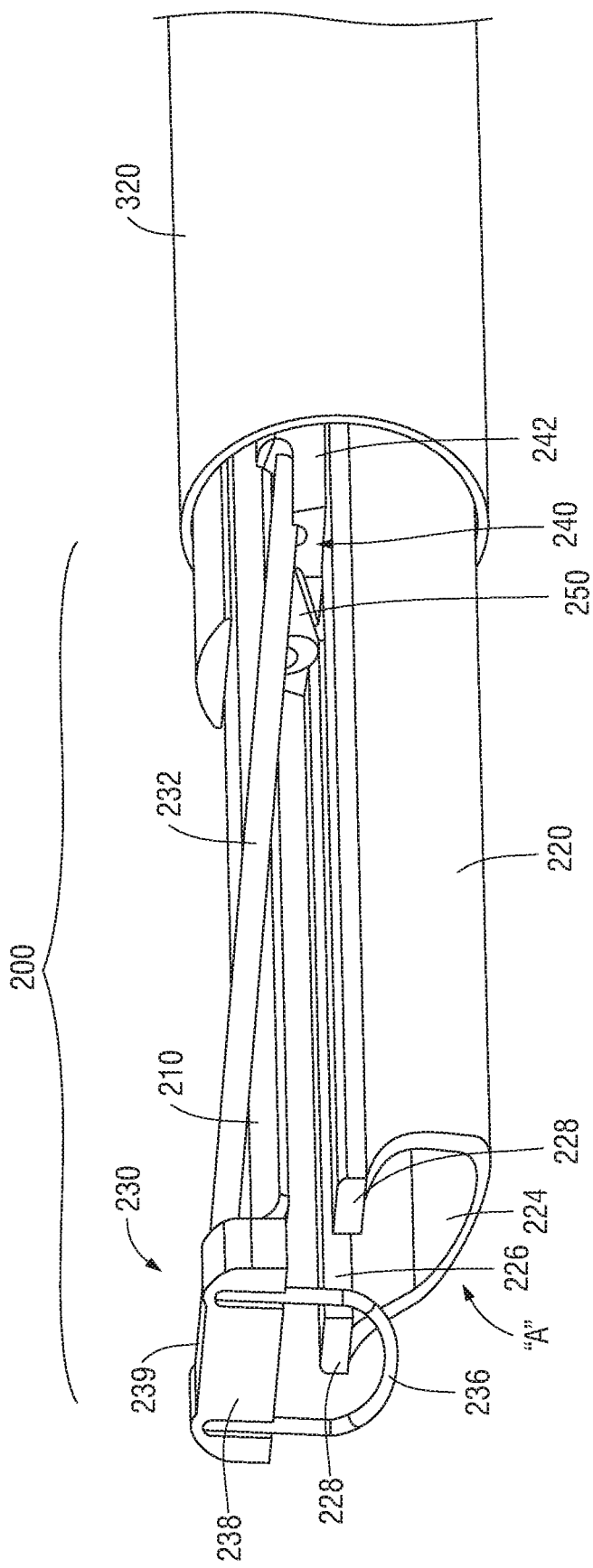
FIG. 6A is a side, perspective view of the distal end of the resectoscope of FIG. 1, disposed in a second position.
Figure 6B:
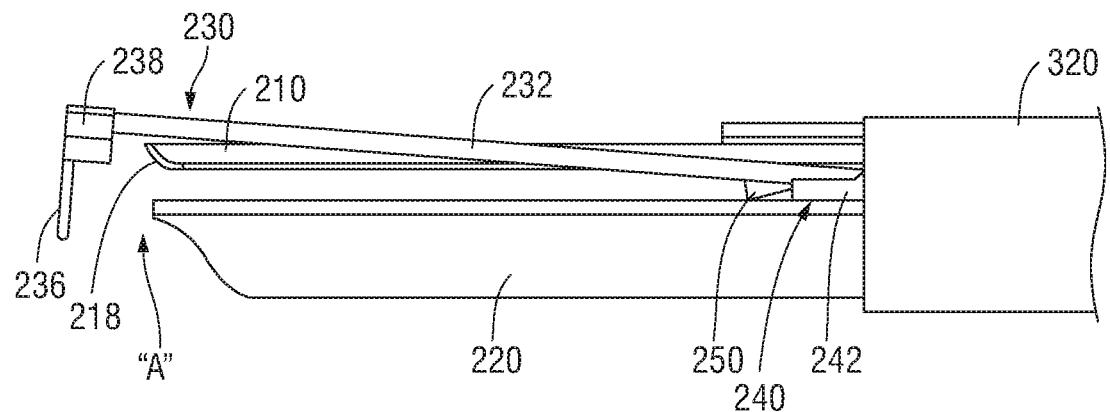
FIG. 6B is a side view of the distal end of the resectoscope of FIG. 1, disposed in the second position.
Figure 6C:
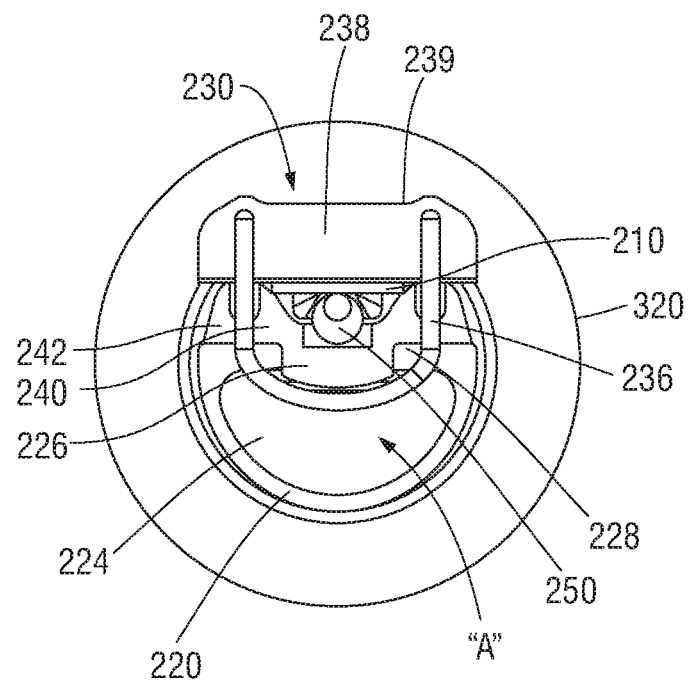
FIG. 6C is a distal end view of the distal end of the resectoscope of FIG. 1, disposed in the second position.

With additional reference to FIGS. 6A-7, during movement of end effector assembly 200 from the retracted position towards the extended position, shaft 220 is extended distally or further distally from sheath assembly 300, and carrier assembly 240 and movable electrode 230 are likewise moved distally relative to plank 210 and sheath assembly 300. More specifically, during movement of end effector assembly 200 from the retracted position to the extended position, spacer 238 of movable electrode 230 is slid distally along plank 210, with a portion of plank 210 received within cut-out 239 of spacer 238. Upon reaching the distal end of plank 210, spacer 238 is urged upwardly to follow rounded lip 218 of plank 210 under the resilient bias of movable electrode 230. As end effector assembly 200 reaches the extended position, spacer 238 clears the distal end of plank 210, thereby allowing movable electrode 230 to fully return to its at-rest position under the resilient bias thereof. As movable electrode 230 returns to the at-rest position, U-shaped loop section 236 of movable electrode 230 is moved upwardly to at least partially traverse the area "A."

Referring to FIGS. 6A-7, in the extended position of shaft 220, spacer 238 is spaced distally from plank 210 and movable electrode 230 is disposed in its at-rest position, wherein the distal portions of longitudinal sections 232, 234 extend above plank 210 and at least portion of U-shaped loop section 236 extends above plank 210. Upon shaft 220 reaching the extended position, U-shaped loop section 236 of movable electrode 230 has fully traversed the lumen extending from channel 224 of shaft 220.

With reference again to FIGS. 1 and 4, resectoscope 10, as noted above, includes a cable assembly 400 having an outer jacket 410 that encloses a power line 420, energy lines 430, and illumination/video connection lines 440. Power line 420, more specifically, is coupled to motor 122 within housing 100 and extends from housing 100 through outer jacket 410 of cable assembly 400. The free end of power line 420 culminates in an electrical plug (not shown) or other suitable connector to enable coupling of power line 420 to a source of power, e.g., power source 510 of generator 500 (FIGS. 8A and 8B), for powering motor 122. However, resectoscope 10 may alternatively be configured as a battery-powered device, e.g., wherein a battery (not shown) disposed within or attached to housing 100 is configured to power motor 122.

Energy lines 430 are configured to connect end effector assembly 200 to an energy source, e.g., high-voltage power supply (HVPS) 520 of generator 500 (FIGS. 8A and 8B), for providing electrosurgical energy thereto. Energy lines 430 extend distally into housing 100 to connect with end effector assembly 200 and proximally from housing 100 through outer jacket 410 of cable assembly 400, ultimately culminating in one or more plugs (not shown) adapted to connect to generator 500 (FIGS. 8A and 8B) or other suitable source of electrosurgical energy. More specifically, positive and negative energy lines 430 are configured to provide first and second potentials to plank 210 (the fixed electrode) and movable electrode 230, respectively, of end effector assembly 200, thus enabling the conduction of energy through tissue disposed between plank 210 and movable electrode 230. This conduction of energy through tissue, along with the movement of movable electrode 230 through tissue, as detailed below, facilitates the resection of tissue, as detailed below.

Illumination/video connection lines 440 extend distally through housing 100 and within or along end effector assembly 200. More specifically, one or more first illumination/video connection lines 440 couples to LED assembly 216 (FIG. 7) to enable illumination of the field of view of endoscope 250, while one or more second illumination/video connection lines 440 couples to endoscope 250 for powering and controlling endoscope 250, and for relaying video and/or still image signals obtained by endoscope 250 to an external display (not shown). Illumination/video connection lines 440 extend proximally from housing 100 through outer jacket 410 of cable assembly 400, ultimately culminating in one or more connectors (not shown) adapted to connect to a suitable external display. Alternatively, endoscope 250 may be configured to wirelessly transmit video and/or still image signals to an external display.

Continuing with reference to FIGS. 1 and 4, resectoscope 10 may include one or more actuators (not shown) disposed on housing 100 and configured to actuate, initiate, and/or control the various features of resectoscope 10. For example, as noted above, an actuator may be mounted on the exterior of housing 100 and coupled to motor 122 to enable selective activation of motor 122 to drive shaft 220 between the proximal and distal positions. Energization of plank 210 (the fixed electrode) and movable electrode 230 may be selectively accomplished via actuation of a separate actuator disposed on housing 100 or remote therefrom, e.g., via a footswitch or a control on the interface of the electrosurgical energy source. Alternatively, the actuator for activating motor 122 may also initiate the supply of energy to plank 210 (the fixed electrode) and movable electrode 230. In some embodiments, energy is supplied to plank 210 (the fixed electrode) and movable electrode 230 only when shaft 220 is translating from the proximal position to the distal position, as described in greater detail below with respect to FIGS. 8A and 8B. With regard to endoscope 250 and LED assembly 216 (FIG. 7), separate and/or combined actuators may be provided on housing 100 or remote therefrom for controlling the various functions thereof.

Turning to FIGS. 5A-7, the assembly, use, and operation of resectoscope 10 is detailed. With additional reference to FIGS. 2 and 3, sheath assembly 300 is initially engaged with housing 100. To engage sheath assembly 300 with housing 100, sheath assembly 300 is slid proximally about end effector assembly 200 until proximal base 310 approximates the distal end of housing 100. More specifically, proximal base 310 of sheath assembly is positioned such that L-shaped slots 314 of proximal base 310 receive posts 114 of housing 100. Once this position has been achieved, sheath assembly 300 is rotated relative to housing 100 to couple sheath assembly 300 with housing 100 via a bayonet-style engagement. With sheath assembly 300 engaged to housing 100, or prior thereto, the distal end of a fluid line (not shown) may be frictionally engaged about port 332, thus enabling irrigation and/or aspiration within sheath assembly 300 and about shaft 220 during the resection procedure. A suction input (not shown) may additionally or alternatively be coupled to the proximal end of shaft 220 to enable suctioning of fluids and/or resected tissue through channel 224 of shaft 220.

Referring again to FIGS. 5A-7, in use, with end effector assembly 200 disposed in the retracted position (FIGS. 5A-5C), resectoscope 10 is inserted into a surgical site such that the exposed distal portion 212 of plank 210 extends over the tissue to be resected. During the insertion, manipulation, and positioning of resectoscope 10, endoscope 250 and/or LED assembly 216 (FIG. 7) may be activated to facilitate visualization within the surgical site.

Once resectoscope 10 is positioned as desired, motor 122 is activated and end effector assembly 200 is energized, e.g., plank 210 is energized to a first potential and movable electrode 230 is energized to a second, different potential. Upon activation of motor 122, shaft 220 is urged from its proximal position to its distal position, wherein shaft extends distally or further distally from elongated tubular sheath 320. As shaft 220 is advanced distally, movable electrode 230 is likewise moved distally. During the initial distal movement of movable electrode 230, U-shaped loop section 236 is maintained in alignment with shaft 220 and, thus, does not traverse the area "A." With energy being conducted between U-shaped loop section 236 of movable electrode 230 and plank 210, this initial distal advancement of U-shaped loop section 236 cuts through tissue along the periphery of area "A," in a longitudinal direction, thereby partially separating the tissue disposed within area "A" from the tissue surrounding area "A."

Upon reaching the extended position of end effector assembly 200, as noted above, movable electrode 230 is resiliently urged upwardly such that U-shaped loop section 236 of movable electrode 230 at least partially traverses area "A," thereby cutting through tissue in a transverse direction, fully separating the tissue disposed within area "A" from surrounding tissue. If suction is applied during the movement of end effector assembly 200 from the retracted position to the extended position, the fully separated tissue, which defines a peripheral dimension that approximates the dimensions of channel 224, can be drawn into channel 224 of shaft 220 via the suction to withdraw the resected tissue from the surgical site.

During the above-detailed resection process, endoscope 250 and/or LED assembly 216 (FIG. 7) may be activated to enable visualization and, thus, help ensure that the appropriate tissue is resected. As noted above, the positioning of endoscope 250 is such that the area of view thereof coincides at least partially with the area "A" and surrounding areas, thus allowing for visualization of tissue being cut and/or tissue that is about to be cut.

In order to resect additional tissue, end effector assembly 200 may be returned to the retracted position and the above-detailed resection process repeated.

Figure 8A:
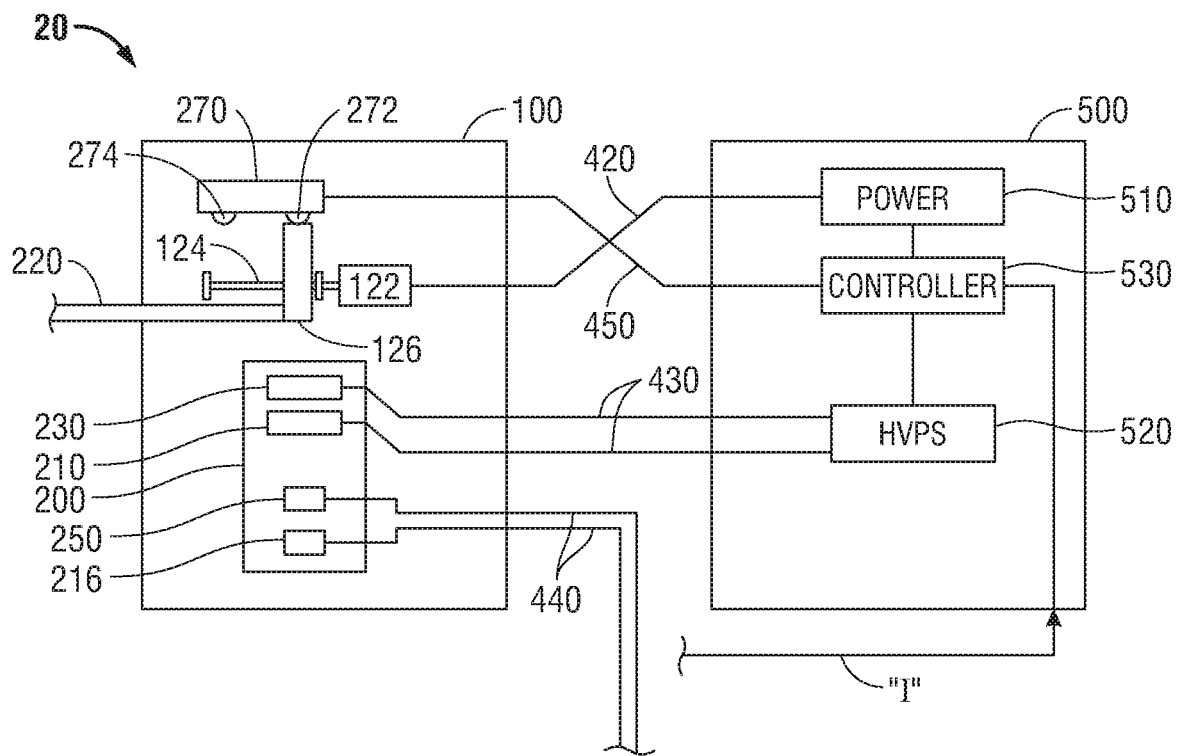
FIG. 8A is a schematic illustration of an electrosurgical system provided in accordance with the present disclosure including the resectoscope of FIG. 1 and a generator, wherein the resectoscope is disposed in the first position.
Figure 8B:
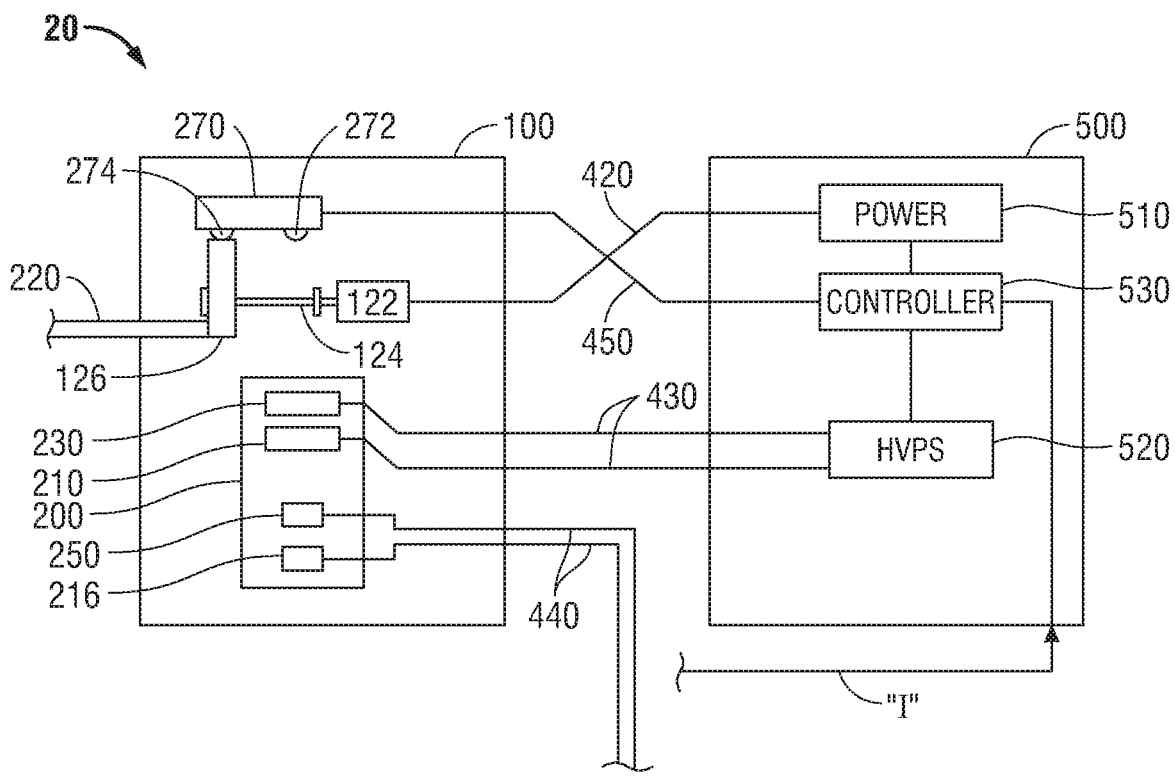
FIG. 8B is a schematic illustration of the electrosurgical system of FIG. 8A, wherein the resectoscope is disposed in the second position.

Turning now to FIGS. 8A and 8B, an electrosurgical system 20 is shown generally including resectoscope 10 and a generator 500. Generator 500 is configured to provide power, electrosurgical energy, and control signals to resectoscope 10 and may be used in conjunction with resectoscope 10 according to any of the embodiments detailed above. In particular, as mentioned above, in some embodiments, electrosurgical energy is supplied to end effector assembly 200, e.g., plank 210 (the fixed electrode) and movable electrode 230, only when shaft 220 is translating from the proximal position to the distal position. In order to provide such a feature, resectoscope 10 further includes a switch assembly 270 operably positioned relative to collar 126 and disposed in communication with generator 500 to control the supply of energy to end effector assembly 200. More specifically, switch assembly 270, as detailed below, is electrically coupled with controller 530 of generator 500 via one or more one or more control lines 450, thus enabling switch assembly 270 to provide feedback to controller 530 to turn ON/OFF the supply of energy from HVPS 520 of generator 500 to end effector assembly 200 via energy lines 430, depending upon the position of collar 126, Switch assembly 270 includes proximal and distal switches 272, 274. Proximal and distal switches 272, 274, together with HVPS 520 of generator 500, form a three-way switching circuit and are positioned adjacent the proximal-most position and distal-most position, respectively, of collar 126. As a result of this configuration, when collar 126 is disposed in the proximal-most position, corresponding to the proximal position of shaft 220, proximal switch 272 is activated. On the other hand, when collar 126 is disposed in the distal-most position, corresponding to the distal position of shaft 220, distal switch 274 is activated.

In use, shaft 220 is initially disposed in the proximal position and, accordingly collar 126 is disposed in the proximal-most position activating proximal switch 272, as shown in FIG. 8A. This initial activation of proximal switch 272 corresponds to an ON condition of switch assembly 270. As such, in this position, upon receipt of an activation input "I" by generator 500, e.g., via actuating an actuator of resectoscope 10, an actuator of generator 500, and/or a remote actuator (e.g., a footswitch), controller 530 directs power source 510 of generator 500 to provide suitable power signals to motor 122 via power line(s) 420 to drive motor 122. Driving of motor 122, as detailed above, translates collar 126 distally and, thus, effects movement of shaft 220 from the proximal position towards the distal position. Controller 530, based upon switch assembly 270 being disposed in the ON condition, also directs HVPS 520 to supply electrosurgical energy to end effector assembly 200 via energy lines 430 to enable energy-based resection as shaft 220 is moved from the proximal position to the distal position.

As shown in FIG. 8B, upon collar 126 reaching the distal-most position, corresponding to the distal position of shaft 220, collar 126 activates distal switch 274, thereby transitioning switch assembly 270 to an OFF condition. When switch assembly 270 is transitioned to the OFF condition, an appropriate signal indicative of the same is relayed to controller 530 via control line(s) 450 to cut-off the supply of electrosurgical energy to end effector assembly 200. Despite stopping the supply of energy, controller 530 continues to direct power source 510 to supply power to motor 122 via power line(s) 420 to drive motor 122, thereby translating collar 126 from the distal-most position back towards the proximal-most position. As such, shaft 220 is returned from the distal position towards the proximal position without supplying electrosurgical energy to end effector assembly 200.

Upon collar 126 returning to the proximal-most position and, correspondingly, shaft 220 returning to the proximal position, proximal switch 274 is activated, once again enabling the supply of electrosurgical energy to end effector assembly 200 as collar 126 and shaft 220 are advanced distally through another actuation stroke, similarly as detailed above. On the other hand, where no further activation input "I" is provided, despite proximal switch 274 being activated, controller 530 cuts-off power supply 510 and HVPS 520 such that shaft 220 is retained in the proximal position and electrosurgical energy supply remains turned off.

As an alternative to the above-detailed continuous mode of operation, controller 530 of generator 500 may be configured to effect a single actuation stroke of collar 126 and shaft 220 upon each activation input "I." In such configurations, a single actuation input "I" to generator 500 effects movement of shaft 220 from the proximal position to the distal position with end effector assembly 200 energized for energy-based tissue resection and, thereafter, return of shaft 220 from the distal position back to the proximal position without supplying energy to end effector assembly 200.

In either the continuous or single-stroke mode of operation, as detailed above, switch assembly 270 and controller 530 operate to supply energy to end effector assembly 200 during deployment, e.g., distal advancement of shaft 220, and to cop the supply of energy to end effector assembly 200 during retraction, e.g., proximal return of shaft 220. This feature not only eliminates the need to have two separate actuators that must be activated in unison, but also helps limit heating of surrounding tissue but limiting the "on-time" of end effector assembly 200. Other suitable feedback and/or switching components for providing these features are also contemplated.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 9:
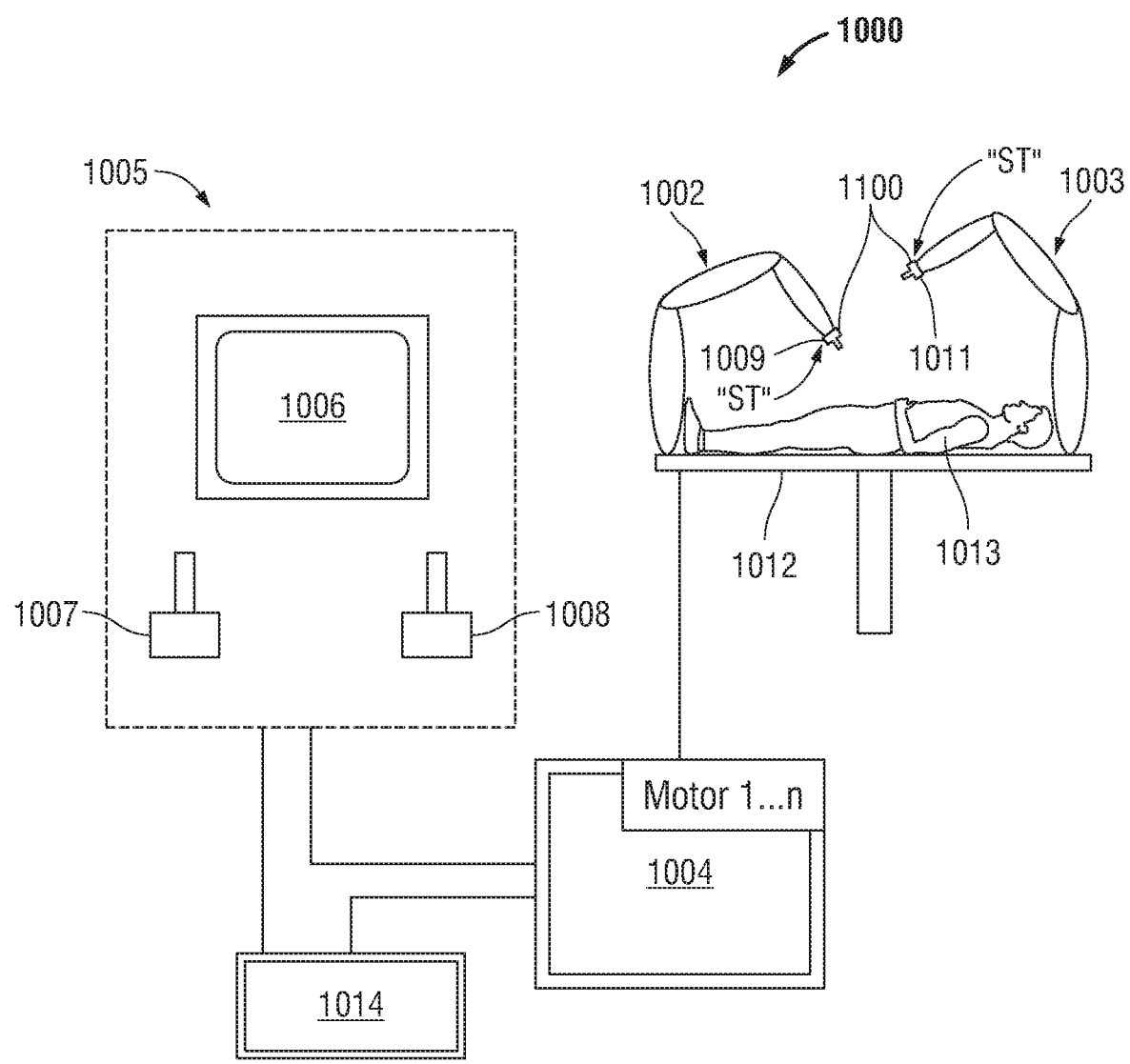
FIG. 9 is a schematic illustration of a robotic surgical system configured for use in conjunction with aspects and features of the present disclosure.

Referring to FIG. 9, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system comprising:
    a resectoscope including:
        an end effector assembly including a fixed electrode and a movable electrode movable relative to the fixed electrode between a first position and a second position;

a longitudinal assembly supporting the movable electrode, the longitudinal assembly including a first arm extending along a first side of the fixed electrode and a second arm extending along a second side of the fixed electrode opposite the first side; and a switch assembly including a first switch and a second switch, the first switch configured such that the first switch is actuated in the first position of the movable electrode, the second switch configured such that the second switch is actuated in the second position of the movable electrode; and a generator including:

an energy source electrically coupled to the fixed electrode and the movable electrode; and a controller in communication with the switch assembly, the controller configured to:

direct the energy source to supply energy to at least one of the fixed electrode or the movable electrode when the movable electrode is moving from the first position to the second position;

inhibit the supply of energy from the energy source to the at least one of the fixed electrode or the movable electrode while the movable electrode is moving from the second position to the first position; and determine a direction of movement of the movable electrode based upon signals received from the first and second switches.

2. The electrosurgical system according to claim 1, wherein the resectoscope further includes a motor configured to drive movement of the movable electrode between the first position and the second position.

3. The electrosurgical system according to claim 2, wherein the generator further includes a power source electrically coupled to the motor, the power source configured to power the motor.

4. The electrosurgical system according to claim 1, wherein movement of the longitudinal assembly relative to the fixed electrode between a proximal position and a distal position moves the movable electrode between the first position and the second position.

5. The electrosurgical system according to claim 4, wherein the resectoscope further includes a drive assembly having a lead screw defining a helical track and a collar disposed about the lead screw and operably coupled to the helical track such that rotation of the lead screw translates the collar about the lead screw, the collar operably coupled to the longitudinal assembly such that rotation of the lead screw moves the longitudinal assembly between the proximal position and the distal position.

6. The electrosurgical system according to claim 5, wherein the helical track is continuous and wherein the lead screw is configured to be rotated in a single direction to translate the collar about the lead screw from a proximal end portion of the lead screw to a distal end portion of the lead screw and back to the proximal end portion of the lead screw.

7. The electrosurgical system according to claim 5, wherein the resectoscope further includes a motor configured to drive rotation of the lead screw.

8. The electrosurgical system according to claim 1, wherein the resectoscope defines a longitudinal axis and wherein the movable electrode is configured to move longitudinally along the longitudinal axis and transversely relative to the longitudinal axis as the movable electrode is moved between the first position and the second position.

9. An electrosurgical system, comprising:

a generator including a power source, an energy source, and a controller; and a resectoscope including:

a drive assembly operably coupled to the power source for enabling driving of the drive assembly;

a shaft coupled to the drive assembly, extending distally from a housing, and configured such that when the drive assembly is driven, the shaft translates relative to the housing between a proximal position and a distal position;

a fixed electrode operably coupled to a first electrical potential of the energy source, the fixed electrode fixed relative to the housing and extending distally from the housing;

a movable electrode operably coupled to a second electrical potential of the energy source, the movable electrode coupled to the shaft such that translation of the shaft relative to the housing between the proximal position and the distal position moves the movable electrode relative to the fixed electrode between a first position and a second position; and a longitudinal assembly supporting the movable electrode, the longitudinal assembly including a first arm extending along a first side of the fixed electrode and a second arm extending along a second side of the fixed electrode opposite the first side, wherein, the controller is configured to permit the energy source to supply energy to the fixed and movable electrodes upon translation of the shaft from the proximal position to the distal position and to inhibit the supply energy to the fixed and movable electrodes during translation of the shaft from the distal position to the proximal position.

10. The electrosurgical system according to claim 9, wherein the resectoscope further includes a switch assembly, and wherein the controller is configured to determine a direction of movement of the shaft based upon signals received from the switch assembly.

11. The electrosurgical system according to claim 10, wherein the switch assembly includes a proximal switch and a distal switch, the proximal switch configured such that the proximal switch is actuated in the proximal position of the shaft, the distal switch configured such that the distal switch is actuated in the distal position of the shaft.

12. The electrosurgical system according to claim 9, wherein the drive assembly includes a motor that is powered by the power source.

13. The electrosurgical system according to claim 9, wherein the resectoscope defines a longitudinal axis, and wherein the movable electrode is configured to move longitudinally along the longitudinal axis and transversely relative to the longitudinal axis as the movable electrode is moved between the first position and the second position.

14. A resectoscope comprising:

a housing;

a drive assembly disposed within the housing and including a collar;

a motor disposed within the housing and configured to move the collar between a proximal position and a distal position;

a switch assembly disposed within the housing and including a proximal switch and a distal switch, the proximal switch configured such that the collar actuates the proximal switch in the proximal position of the collar, the distal switch configured such that the collar actuates the distal switch in the distal position of the collar;

a fixed electrode adapted to connect to a first electrical potential, the fixed electrode fixed relative to the housing;

a movable electrode adapted to connect to a second electrical potential, the movable electrode coupled to the collar such that translation of the collar relative to the housing between the proximal position and the distal position moves the movable electrode relative to the fixed electrode between a first position and a second position; and a longitudinal assembly supporting the movable electrode, the longitudinal assembly including a first arm extending along a first side of the fixed electrode and a second arm extending along a second side of the fixed electrode opposite the first side, wherein the proximal and distal switches control supply of energy to the fixed and movable electrodes such that energy is permitted to be supplied to the fixed and movable electrodes when the movable electrode is moving from the first position to the second position and energy is inhibited from being supplied to the fixed and movable electrodes while the movable electrode is moving from the second position to the first position.

15. The resectoscope according to claim 14, wherein the drive assembly further includes a lead screw defining a helical track, the collar disposed about the lead screw and operably coupled to the helical track such that rotation of the lead screw translates the collar about the lead screw.

16. The resectoscope according to claim 15, wherein the helical track is continuous and wherein the lead screw is configured to be rotated in a single direction to translate the collar about the lead screw from a proximal end portion of the lead screw to a distal end portion of the lead screw and back to the proximal end portion of the lead screw.

17. The resectoscope according to claim 14, wherein the resectoscope defines a longitudinal axis and wherein the movable electrode is configured to move longitudinally along the longitudinal axis and transversely relative to the longitudinal axis as the movable electrode is moved between the first position and the second position.

* * * * *